United States Patent [19]
Torrens et al.

[11] Patent Number: 5,576,181
[45] Date of Patent: Nov. 19, 1996

[54] PROCESS FOR SELECTIVE REMOVAL OF SALIVARY α-AMYLASE AND ASSAY FOR PANCREATIC α-AMYLASE

[75] Inventors: David J. Torrens, Maidstone; Howard J. Marriage, Wadhurst, both of Great Britain

[73] Assignee: Genzyme Ltd., Haverhill, England

[21] Appl. No.: 793,060

[22] Filed: Nov. 15, 1991

[30] Foreign Application Priority Data

Nov. 16, 1990 [GB] United Kingdom ............... 9024970

[51] Int. Cl.$^6$ ................................................. G01N 33/573
[52] U.S. Cl. ........................ 435/7.4; 435/810; 435/961; 435/962; 436/526; 436/539; 436/823; 436/824; 530/388.26; 530/391.1; 530/413
[58] Field of Search ..................... 435/7.4, 70.21, 435/172.2, 810, 962, 961; 436/526, 539, 541, 548, 177, 178, 823; 530/388.26, 391.1, 413, 845

[56] References Cited

U.S. PATENT DOCUMENTS 4,554,088  11/1985  Whitehead et al. ................. 252/62.54
4,939,082  7/1990  Naujoks et al. ......................... 435/7.4

OTHER PUBLICATIONS

Mifflin, T. E. et al, "Rapid Quantitative, Specific Measurement of Pancreatic Amylase in Serum with Use of a Monoclonal Antibody", Clin. Chem. 31(8) pp. 1283–1288, 1985.

Bruns, D. E. et al, "Appendix: Production and Characterization of a Monoclonal Antibody to Distinguish Human Pancreatic and Salivary Amylase", Clin. Chem. 31(8) pp. 1286–1288, 1985.

Gerber, M. et al, "A Monoclonal Antibody That Specifically Inhibits Human Salivary α–Amylase", Clin. Chem. 33(7) pp. 1158–1162, 1987.

Ito, K. et al, "Preparation of Human Salivary α–Amylase Specific Monoclonal Antibody", J. Biochem. 97(5) pp. 1357–1362, 1985.

Hiroishi, S. et al, "Differnetial Assay of Salivary and Pancreatic α–Amylase in Serum and Urine, with Use of Monoclonal Antibody to Human Salivary Amylase Immobilized on Bacterial Cell Wall", Cli. Chem. 33(7) pp. 1235–1236, 1987.

Primary Examiner—James C. Housel
Assistant Examiner—Gary Tanigawa
Attorney, Agent, or Firm—William G. Gosz

[57] ABSTRACT

Inter alia, a process for the selective removal of salivary α-amylase from a sample comprising salivary α-amylase and pancreatic α-amylase characterized in that there is used a monoclonal antibody against salivary α-amylase, which is immobilized or is coupled to a physically separable or seperate support and which exhibits a binding affinity towards salivary α-amylase of at elast $1\times10^7$ l/m and a cross-reactivity with pancreatic α-amylase of less than 1% is disclosed. The remaining pancreatic α-amylase may be assayed.

6 Claims, No Drawings

PROCESS FOR SELECTIVE REMOVAL OF SALIVARY α-AMYLASE AND ASSAY FOR PANCREATIC α-AMYLASE

This invention relates to a process for the selective removal of salivary α-amylase and to an assay for pancreatic α-amylase.

The human pancreas contains a number of digestive enzymes, such as amylase, lipase and trypsin. Inflammation of this organ, such as in acute or chronic pancreatitis, may cause release of such enzymes into the bloodstream, where the increased activities thereof may be detected.

Serum α-amylase is the most widely used clinical indicator of inflammation of or injury to the pancreas. It is of particular value in the differential diagnosis of acute abdominal pain of which acute pancreatitis may be the cause.

Amylase is usually determined by its ability to degrade a substrate generating a product which may be measured in a spectrophotometer. Such assays measure not only pancreatic-type amylase which is derived from the pancreas, but also salivary-type amylase, which is found in a number of tissues including salivary glands, testes, ovaries, fallopian tubes, striated muscle, lung and adipose tissue. Consequently, non-pancreatic disease may result in an elevation of total serum amylase activity.

It is an object of the present invention to provide for the selective physical removal of salivary α-amylase from a sample comprising both α-amylase isozymes, so as to allow the measurement of remaining pancreatic amylase if desired.

Both the salivary and pancreatic enzymes are α-amylase (E.C.3.2.1.1.) which degrades 1,4-D-glucoside-linked oligo- and poly-saccharides by hydrolysis of 1,4-α-glucoside bonds to generate maltose and malto-oligosaccharides. At present, there is no effective way to distinguish between these isozymes in terms of mode of action, substrate specificity or end products. Although the primary structures of the two isozymes are very similar, they may be separated by electrophoresis, column chromatography, isoelectric focusing and radioimmunoassay, for example. However, these methods are slow and complex to perform.

It is known that salivary and pancreatic amylases are differentially inhibited by certain wheat germ lectins. Judicious use of lectin concentration allows the inhibition of the greater part of the salivary amylase activity, while not affecting most of the pancreatic amylase activity. However, this approach is not widely used due to its lack of specificity.

Another known inhibition method uses two monoclonal antibodies "synergistically" to inhibit salivary amylase. The main limitation of this procedure is that it is not possible to measure both total and pancreatic amylase using the same kit, as the vial containing the antibodies also contains α-glucosidase, which is necessary for the development of a coloured product. It has been suggested (Cummings and Fraser, Ann Clin Biochem, 26(4):335–340;1989), that the initial diagnosis of acute pancreatitis be established using pancreatic amylase, while the progress of the disease is followed by the measurement of total serum amylase. The use of two different reagent systems would generally be regarded as wasteful of reagent and unnecessarily costly to the user.

An approach was desired which allowed the use of a laboratory's existing α-amylase detection methodology, together with an optional step for the performance of a pancreatic-specific assay.

Conventional extraction assays would use tight binding molecules, such as antibodies raised against the species to be removed. These would generally be bound to a solid phase requiring a process, such as column chromatography, which is a time-consuming manual technique. Alternatively, the antibodies could be combined with a precipitating species, such as protein A, or a second antibody, which would involve the use of a centrifuge to separate the bound non-required species from the species for analysis in free solution.

A separation system requiring no involvement of chromatography or centrifugation which may be performed rapidly in an emergency assay may be envisaged where the antibody is immobilised to very large or magnetic particles. Generally, the present invention concerns the use of monoclonal antibodies immobilised or coupled to physically-separable or separate supports to facilitate the removal of one antigen from a system so that another may be determined without significant interference.

In one embodiment, the present invention provides a process for the selective removal of salivary α-amylase from a sample comprising salivary α-amylase and pancreatic α-amylase characterised in that there is used a monoclonal antibody against salivary α-amylase, which is immobilised or is coupled to a physically separable or separate support and which exhibits a binding affinity towards salivary α-amylase of at least $1\times10^7$ l/M and a cross-reactivity with pancreatic α-amylase of less than 1%.

Such physical removal of salivary α-amylase may, if desired, be followed by the determination of remaining pancreatic α-amylase, but may, of course, be an end in itself.

Preferably, the monoclonal antibody exhibits a binding affinity towards salivary α-amylase of at least $1\times10^8$ l/M and a cross-reactivity with pancreatic α-amylase of less than 0.5%. More particularly, the monoclonal antibody is that identified as 5/262 (ECACC 90031302) or 5/330 (ECACC 90031306).

The monoclonal antibody is generally immobilised on a membrane or in a discrete layer or is coupled to a paddle, to a tube wall or to a particle, which may be separated by magnetism, centrifugation or filtration.

In another embodiment, the present invention provides a kit for the selective removal of salivary α-amylase characterised in that it comprises such a monoclonal antibody. Such a kit in accordance with the present invention may further comprises means for determining pancreatic α-amylase. Of course, such are generally known.

In a further embodiment, the present invention provides a monoclonal antibody against salivary α-amylase characterised in that it exhibits the properties defined above and is preferably that identified as 5/262 (ECACC 90 031 302) or 5/330 (ECACC 90 031 306). Such may also be provided in accordance with the present invention in immobilised or coupled form as a reagent or even a "device". ECACC 90031302 and ECACC 90031306 have been deposited under the terms of the Budapest Treaty with the Public Health Laboratory Service, Centre for Applied Microbiology and Research, Porton Down, Salisbury, Wilts. SP4 0JG, U.K.

The production of such antibodies and the application thereof is generally conventional, but the selection is important.

An appropriate antibody against salivary amylase, for example, will bind rapidly and then remove it from solution, thus allowing, in this case, pancreatic amylase remaining in solution to be measured.

The key component of such a system would be regarded as the antibody, the development of a highly specific tight binding monoclonal antibody being preferred. A procedure was undertaken to obtain monoclonal antibodies suitable for this technique using analytical procedures designed to generate and select for those having the tightest binding and lowest cross-reactivity. It is well known that the process for generating monoclonal antibodies of a particular type will result in many thousands of cell lines. Thus, the criteria for selection of suitable cell lines is an important part of the product development.

Twenty thousand cell lines were generated during the course of this work. Although many of these produced antibodies to amylase, only twenty-four were specific for salivary amylase. The use of a radioimmunoassay allowed further selection on the grounds of binding affinities and more accurate cross-reactivity measurements.

Initially, two particularly tight binding monoclonal antibodies that were specific for salivary amylase were produced, referred to herein as 5/262 and 5/330, (90031302 and 90031306 respectively.) These had binding affinities towards salivary amylase of $3 \times 10^8$ l/M and $2 \times 10^{10}$ l/M, and cross-reactivities towards pancreatic amylase of less than 0.5% and less than 0.1%, respectively. Thus, antibody 5/330 showed superior results for both binding affinity and specificity.

The two antibodies were coupled to a number of solid phase supports using different conjugation methods. Surprisingly, in each case where a direct comparison was made, the antibody with the weaker binding affinity in free solution showed superior ability to remove salivary amylase when bound to a solid phase. The cross-reactivities towards pancreatic amylase also behaved in an unexpected fashion. The antibody with the lowest cross-reactivity bound more pancreatic amylase when it was immobilised.

When using antibody-coupled beads to remove salivary amylase from serum it was found that results could be further improved by the addition of compounds, such as an antifoam agent, a bacteriostat and agents to reduce non-specific binding. Such is well within the competence of one skilled in the art.

The following illustrates the present invention:

Firstly, the development of monoclonal antibodies:

Balb/c mice were immunised with immunopurified salivary amylase (purchased from Aalto Bioreagents, Dublin, Eire.) 50 µg of this material in Freund's complete adjuvant was injected via the intraperitoneal route into the mice. After three, six and nine weeks, the injections were repeated, but on these occasions Freund's incomplete adjuvant was used. On week eleven, 50 µg of the antigen in saline was injected intravenously. After a further three days, the animals were killed and the spleens removed.

Cell fusion was performed essentially as described by Galfre and Milstein (Methods in Enzymology, 73:3–46;1981). Spleens from the immunised animals were removed and gently homogenised until all the cells had been removed from the membrane. The spleen cell suspension was washed three times in Dulbecco's modified Eagle's medium (DMEM), supplemented with L-glutamine, penicillin/streptomycin and 10% foetal calf serum (FCS). After re-suspension in a known volume, the cells were counted in a haemocytometer using methyl violet citric acid stain.

The myeloma cell line used was NSO (uncloned), obtained from the Medical Research Council Laboratory of Molecular Biology in Cambridge, UK. The myeloma cells, in logarithmic growth phase, were washed in DMEM and counted in a haemocytometer using phase contrast microscopy.

Spleen cells ($1 \times 10^8$) were mixed with myeloma cells ($7 \times 10^7$), centrifuged and the liquid removed. The resultant cell pellet was placed in a 37° C. water bath. Over a period of 1 minute, 1 ml of a 50% (w/v) solution of polyethylene glycol 1500 (PEG) in saline HEPES buffer, pH 7.5, was added and the mixture gently stirred for 1½ minutes. Over a period of 5 minutes, 50 ml of serum-free DMEM was added, followed by centrifugation. The supernatant was discarded and the cell pellet re-suspended in 10 ml of DMEM containing 18% FCS. The resultant cell suspension was placed in each of 960 wells in an amount of 10 µl per well in standard multiwell tissue culture plates. Each well contained 2 ml of standard HAT medium (hypoxanthine, aminopterin and thymidine), and a feeder layer of Balb/c macrophages at a concentration of $5 \times 10^4$ macrophages per well. The wells were maintained at 37° C. under 9% $CO_2$ air at approximately 90% humidity.

Screening for production of monoclonal antibodies was by solid phase immunoassay. Purified salivary and pancreatic amylase (Aalto Bioreagents) were adsorbed onto Nunc Maxisorp microtitre plates in high pH buffer. The plates were blocked with bovine serum albumin and then washed. Mouse antibody binding was detected using a goat anti-mouse second antibody convalently coupled to horseradish peroxidase. Ortho-phenylene diamine was used as the substrate for the peroxidase.

From those wells which contained cells producing antibodies specific to the target antigen, cells were removed and cloned by the conventional dilution cloning procedure. At each stage, antibody activity was monitored by enzyme immunoassay.

Antibody binding was further assessed by radioimmunoassay. Salivary amylase was labelled with $^{125}$I by the chloramine T procedure to a specific activity of 70 µCi/µg. In the assay, antibody-bound tracer was separated from free tracer by donkey anti-mouse antibodies bound to a cellulose bead solid phase. From the radioimmunoassay, the percentage cross-reactivity with pancreatic amylase activity was obtained and, after Scatchard analysis, the binding affinities of the antibodies were determined.

Two cell lines were found to produce tight binding monoclonal antibodies specific for salivary amylase and these were designated 5/262 and 5/330. The binding affinities for salivary amylase were found to be $3 \times 10^8$ l/M and $2 \times 10^{10}$ l/M, respectively. Therefore, in free solution, antibody 5/330 has a far superior binding affinity for salivary amylase. The cross-reactivities of these two antibodies towards pancreatic amylase were less than 0.5% and less than 0.1%, respectively.

To purify the antibodies, tissue culture fluid was first passed through a 0.2 µm filter. To separate the antibodies, the fluid was pumped onto a column of immobilised protein A. After elution using a pH 3.5 glycine buffer, the antibody was dialysed into phosphate-buffered saline, pH 7.4.

Secondly, the coupling of antibodies to 6.4 mm polystyrene beads:

Polystyrene beads having a diameter of 6.4 mm and coated with hydrazide groups were purchased from Life Science Laboratories (UK) Ltd.

25 beads were gently shaken with 5 ml of 12.5% glutaraldehyde in 0.1M sodium phosphate buffer, pH 7.0, for 2 hours at room temperature. The beads were next washed in a Buchner funnel with 100 ml of deionised water and then with 50 ml of 0.1M sodium phosphate buffer, pH 6.0. The glutaraldehyde-activated beads were added to 2.5 mg of antibody in 5 ml of the phosphate buffer at pH 6.0, followed by the addition of approximately 1 mg of sodium cyanoborohydride. After gentle mixing at room temperature overnight, the antibody-coupled beads were washed with 100 ml of phosphate buffer, pH 6.0, and then with 50 ml of 0.1M sodium bicarbonate. A further gentle mixing of the beads was performed with 5.0 ml of 0.1M sodium bicarbonate containing approximately 1 mg of sodium borohydride. After a final washing with 100 ml of 0.1M sodium carbonate and 100 ml of deionised water, the beads were dried and stored at 4° C. prior to use.

The polystyrene beads coupled with antibody 5/262 were compared with those coupled with antibody 5/330 by incubating a single bead with 100 μl of either salivary or pancreatic amylase at an activity of 1000 u/l. The incubations were performed at room temperature for 1 hour. At the end of this period, 20 μl samples of the remaining liquid were assayed for amylase activity by a standard method.

The beads coupled with antibody 5/262 left 8% of the salivary amylase and 89% of the pancreatic amylase in solution. In comparison, 21% of the salivary amylase activity and 89% of the pancreatic amylase was left after incubation with the 5/330-coupled beads.

Thirdly, the coupling of antibodies to Dynabeads M-280:

Dynabeads M-280 tosyl-activated are uniform superparamagnetic polystyrene beads having a diameter of 2.8 μm. The surface of these beads is pre-activated with a p-toluene-sulphonyl chloride treatment. This material was purchased from Dynal (UK) Ltd.

1 ml of a 10 mg/ml bead suspension was washed three times with phosphate-buffered saline. These and all subsequent washes were performed by mixing with the washing agent, collecting the beads magnetically, discarding the supernatant and re-suspending the pellet with more wash buffer.

After the last of these washes, the pellet was re-suspended with 0.5 ml of 50 mM borate buffer, pH 9.5. A solution of antibody at a concentration of 800 μg/ml was prepared in 50 mM borate buffer, pH 9.5, and then 500 μl of this was mixed with the re-suspended beads. This mixture was vigorously shaken at room temperature for 48 hours.

The antibody-coated beads were then washed three times, 10 minutes each time, with phosphate-buffered saline containing 0.1% bovine serum albumin. After another wash for 30 minutes, the beads were left to wash a last time overnight at 4° C., again in the same wash buffer. The coated beads were stored in the same buffer at 4° C. before being tested.

The beads coated with antibody 5/262 were compared with those coated with antibody 5/330 for their ability to remove salivary and pancreatic amylases from solution. 20 μl of a 20 mg/ml suspension were mixed with 100 μl of salivary or pancreatic amylase at an activity of 1000 u/l. After being left to stand for 5 minutes, the tubes containing the suspensions were placed over a magnet for 2 minutes. This drew the beads downwards to form a pellet, leaving a clear supernatant above. 20 μl aliquots of the supernatant were taken for measurement of the residual amylase activity.

Dynabeads coupled with antibody 5/262 were found to have left 6% of the salivary amylase and 85% of the pancreatic amylase activity in the supernatant. However, the antibody 5/330-coated beads had left 12% of the salivary and 76% of the pancreatic enzyme in the unbound fraction.

Firstly, a preferred coupling of the antibody 5/262 to Biomag 4100 particles.

Biomag magnetic beads are super-paramagnetic particles of iron oxide coated with polymeric silane to provide sterically unencombered functional groups. (The Biomag 4100 particles are obtainable from Advanced Magnetics, Cambridge, Mass., USA, and are more fully described in U.S. Pat. No. 4,554,088.)

300 ml of a 50 mg/ml sispension of particles were washed four times with 0.01M pyridine, pH 6.0. These and all subsequent washes were performed by mixing with washing agent, collecting the beads magnetically, discarding the supernatant and re-suspending the pellet in the next solution.

600 ml of 5% v/v glutaraldehyde were added to the particle pellet which was re-suspended and transferred to a 1 liter plastic bottle. This was mixed for 3 hours at room temperature on a roller mixer.

The activated beads were washed with 4×500 ml 0.01M pyridine, pH 6.0.

150 mg of antibody in 0.01M pyridine, pH 6.0, were mixed with the beads, resulting in a total volume of 150 ml. This was mixed overnight at room temperature. The particles were washed with 2×500 ml 0.01M pyridine, pH 6.0.

To block unreacted groups, the particles were mixed with 700 ml of 1M ethanolamine, pH 8.0, for 3 hours at room temperature. To ensure complete removal of non-covalently bound antibody, the beads were subjected to a stringent washing protocol. The particles were first wahsed with 4×500 ml 50 mM glycine buffer, pH 10.0, with 1M NaCl and 0.01% w/v bronopol.

The follwoing day, the particles were re-washed twice with the glycine NaCl buffer and then mixed with the same buffer for 3 hours. After four washes with 1M ethanolamine, pH 8.0, the particles were mixed overnight in the ethanolamine. The particles were then washed four times with phosphate-buffered saline containing 0.01% w/v bronopol and 0.1% w/v polypropylene glycol, and then re-suspended in the same buffer mixture to 5 mg/ml.

The beads were incorporated as part of the following reagent:
5 g/l beads
0.01% w/v bronopol
0.1% w/v polypropylene glycol
1.2M urea
in phosphate-buffered saline.

Bronopol was used to prevent bacterial growth, polypropylene glycol to prevent frothing during mixing with sample and urea to increase the recovery of pancreatic amylase by reducing non-specific binding.

Magnetic separation time was determined by the mixing of 100 μl particles suspension with 100 μl of 1000 u/l salivary amylase in phosphate-buffered saline containing 1% BSA in 1.5 ml tubes. After standing for 10 minutes at room temperature, the tubes were placed in a rack containing magnets composed of neodymium iron and boron for varying lengths of time. The removal of salivary amylase at greater than 98% occurred by 1 minutes as determined by analysis of the supernatant for amylase activity. This was performed using a benzylidine-blocked maltoheptaoside paranitrophenyl substrate using a kinetic microtitre plate analyser.

The effect of incubation time at room temperature was determined using the reagent described above. 100 μl of 1000 u/l salivary and 100 μl of 1000 u/l pancreatic amylase test solution were mixed with 100 μl of reagent and allowed to stand for varying periods of time, followed by a 1 minute magnetic separation. The supernatant was analysed for the activity of pancreatic or salivary amylase. After 3 minutes, 97.6% of the salivary amylase was removed by the reagent, which increased to 98.2% with a 5 minute incubation. A further small increase in removal to 98.9% was observed after a 60 minute incubation. The recovery of pancreatic amylase was 88% at 3 minutes, 5 minutes and 60 minutes.

The capacity of the reagent system was tested by the incubation of 100 μl of various activities of either salivary or pancreatic amylase with 100 μl of reagent. The incubation time was 5 minutes with a separation time of 1 minute. At 1000 u/l, 2000 u/l and 3000 u/l of each isoenzyme activity the removal of salivary amylase was 98.0%, 97.2% and 96.7%, respectively, and the recovery of pancreatic amylase was 88%, 89% and 88%, respectively.

The within and between batch precision was tested using human serum and for the between batch experiment the quality control serum Precinorm and Precipath were included. The results are tabulated below.

A correlation using the reagent described above was performed against a pancreatic amylase methodology obtained from Boehringer Mannheim (Cat. No. 1005 006). The correlation coefficient obtained with 100 patients' sera was 0.996 with the equation for regression analysis: y=1.072x−60.1.

| WITHIN BATCH PRECISION | | | | |
|---|---|---|---|---|
| | MINIMUM (U/L) | MAXIMUM (U/L) | n | CV |
| HIGH POOL | 1,422 | 1500 | 19 | 1.37 |
| MEDIUM POOL | 414 | 432 | 20 | 1.55 |
| LOW POOL | 270 | 288 | 20 | 1.68 |

| BETWEEN BATCH PRECISION | | | | |
|---|---|---|---|---|
| | MINIMUM (U/L) | MAXIMUM (U/L) | n | CV |
| HIGH POOL | 1,446 | 1.596 | 21 | 2.437 |
| MEDIUM POOL | 420 | 476 | 21 | 2.972 |
| LOW POOL | 258 | 306 | 21 | 4.293 |
| PRECINORM | 375 | 411 | 21 | 2.806 |
| PRECIPATH | 720 | 774 | 21 | 2.138 |

We claim:

1. A process for the selective removal of salivary alpha-amylase from a sample comprising salivary alpha-amylase and pancreatic alpha-amylase, said process comprising:

contacting the sample with a monoclonal antibody specific for salivary alpha-amylase and not pancreatic alpha-amylase, said antibody being identified as ECACC 90031302 and being coupled to a superparamagnetic support;

allowing the antibody to bind to the salivary alpha-amylase, forming a complex, and removing the complex from the sample.

2. A process as claimed in claim 1 wherein the process further comprises the determination of remaining pancreatic α-amylase.

3. A monoclonal antibody against salivary alpha-amylase identified as ECACC 90031302.

4. A kit for the selective removal of salivary α-amylase characterised in that the kit comprises a monoclonal antibody as defined in claim 3.

5. A kit as claimed in claim 4 wherein the kit further comprises means for determining pancreatic α-amylase.

6. A kit as claimed in claim 4 or claim 5 wherein the kit also comprises an antifoam agent and/or a bacteriostat and/or an agent to reduce non-specific binding.

* * * * *